United States Patent [19]
Edwards et al.

[11] Patent Number: 5,601,591
[45] Date of Patent: Feb. 11, 1997

[54] STENT FOR USE IN PROSTATIC URETHRA, APPARATUS AND PLACEMENT DEVICE FOR SAME AND METHOD

[75] Inventors: Stuart D. Edwards, Los Altos; Ronald G. Lax, Grass Valley, both of Calif.

[73] Assignee: Vidamed, Inc., Menlo Park, Calif.

[21] Appl. No.: 310,976

[22] Filed: Sep. 23, 1994

[51] Int. Cl.[6] ............................................. A61M 29/00
[52] U.S. Cl. ......................... 606/198; 606/191; 606/108
[58] Field of Search ..................................... 606/195, 191, 606/194, 108, 109, 198; 128/898

[56] References Cited

U.S. PATENT DOCUMENTS

| | | | |
|---|---|---|---|
| 3,868,956 | 3/1975 | Alfidi et al. | |
| 4,553,545 | 11/1985 | Maass et al. | 128/341 |
| 4,606,330 | 8/1986 | Bonnet | 128/7 |
| 4,893,623 | 1/1990 | Rosenbluth | |
| 5,059,211 | 10/1991 | Stack et al. | |
| 5,100,423 | 3/1992 | Fearnot | 606/159 |
| 5,160,341 | 11/1992 | Brenneman et al. | 606/198 |
| 5,201,757 | 4/1993 | Heyn et al. | 606/198 |
| 5,249,585 | 10/1993 | Turner et al. | 607/99 |
| 5,258,020 | 11/1993 | Froix | |
| 5,306,286 | 4/1994 | Stack et al. | |
| 5,320,617 | 6/1994 | Leach | 606/15 |
| 5,409,453 | 4/1995 | Lundquist et al. | 604/22 |
| 5,476,505 | 12/1995 | Limon | 623/1 |

FOREIGN PATENT DOCUMENTS

0516189B1  9/1994  European Pat. Off.

OTHER PUBLICATIONS

Dotter, Charles T; "Transluminally–placed Coilspring Endarterial Tube Grafts"; *Long–Term Patency in Canine Popliteal Artery*; Investigative Radiology, Sep.–Oct., 1969, pp. 329–332.
Narciso, H. L.; Abstract of WO 9415583 for Bio–absorbable, biogenic, medicament dispensing implant.
Demane C; Schwarz R.; Abstract of EP 605974 for Post–operative nasal stent to prevent adhesion and scar formation.
Igaki, K.; Abstract of WO 9405364 for Vessel stent for insertion into e.g. blood vessel.
Igaki K; Tamai, H.; Abstract of WO 9215342 for Improved stent for vessels.
Stack, R. S.; Clark, H. G., and Walker, W. F.; Abstract of WO 9117789 for An intraluminal stent.

*Primary Examiner*—Michael Powell Buiz
*Assistant Examiner*—Patrick W. Rasche
*Attorney, Agent, or Firm*—Flehr, Hohbach, Test, Albritton & Herbert

[57] ABSTRACT

A stent for introduction into a portion of a urethra in a body of a patient. The urethra extends through a prostate and is formed by a wall having a diameter. The stent includes a longitudinally-extending body made from a material adapted for absorption by the body of the patient. The longitudinally-extending body has an expanded condition in which the body has a predetermined diameter greater than the diameter of the portion of the urethra extending through the prostate. The longitudinally-extending body is formed with a plurality of coils along the length thereof adapted to engage the wall of the urethra when the longitudinally-extending body is in the expanded condition. The longitudinally-extending body is provided with spaces between the coils to permit the wall of the urethra to extend therein and serve to anchor the longitudinally-extending body to the wall.

18 Claims, 3 Drawing Sheets

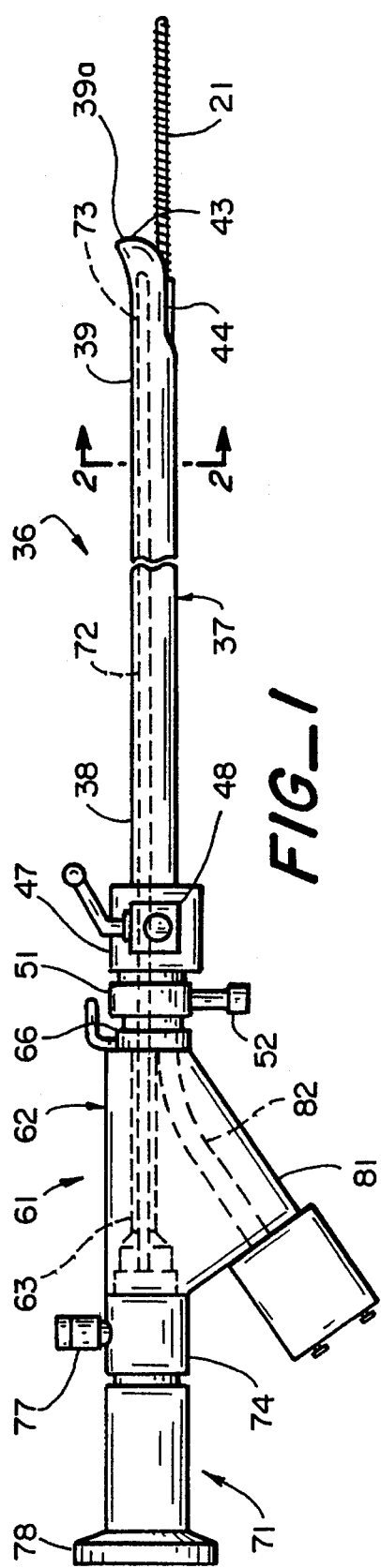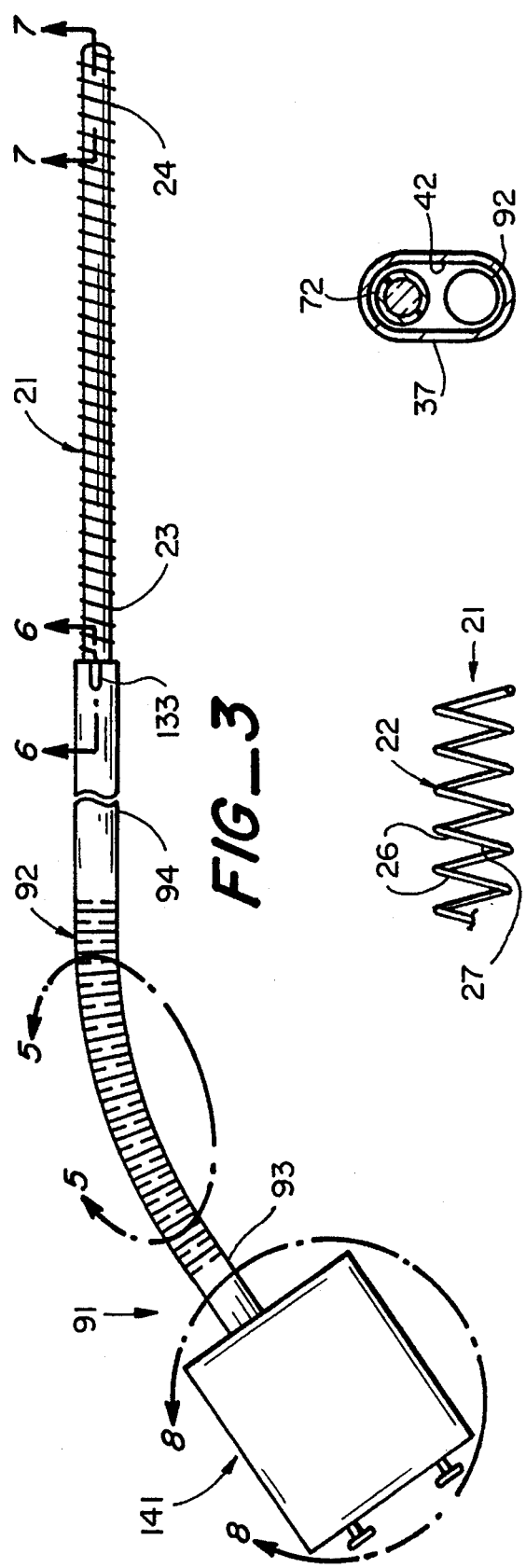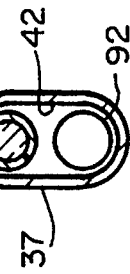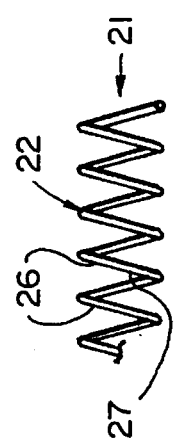

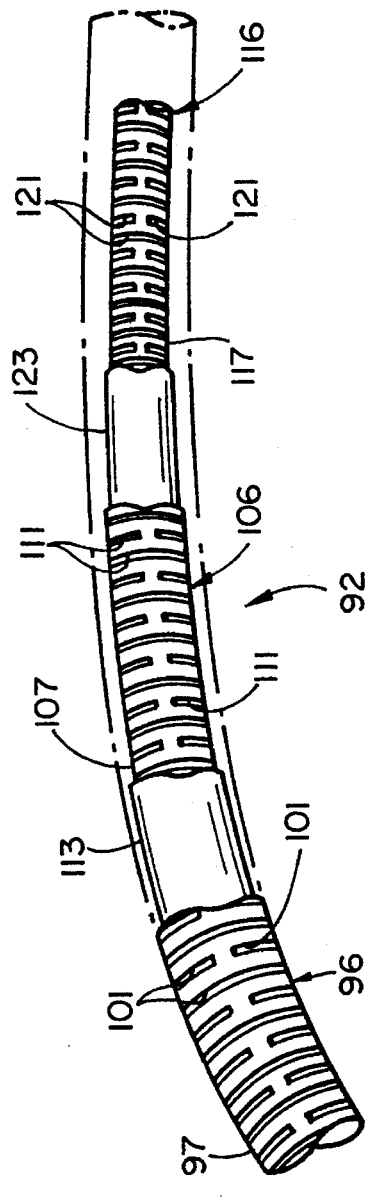
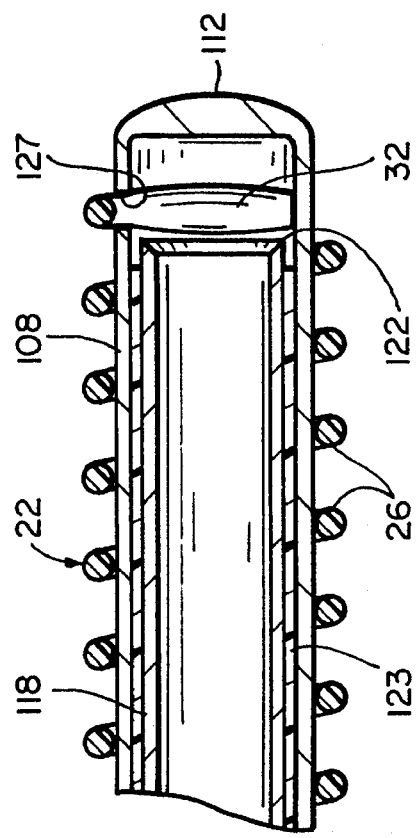
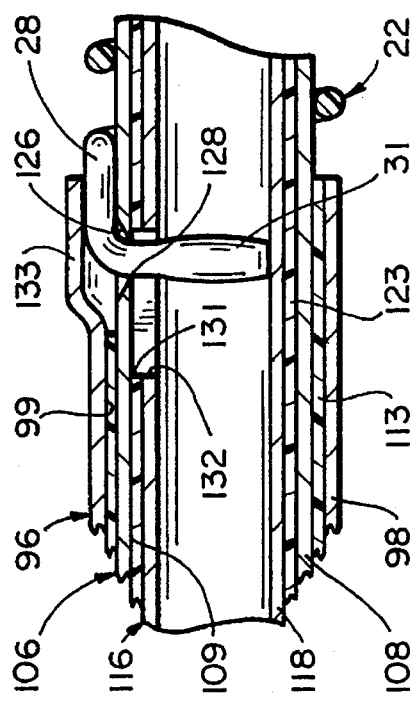

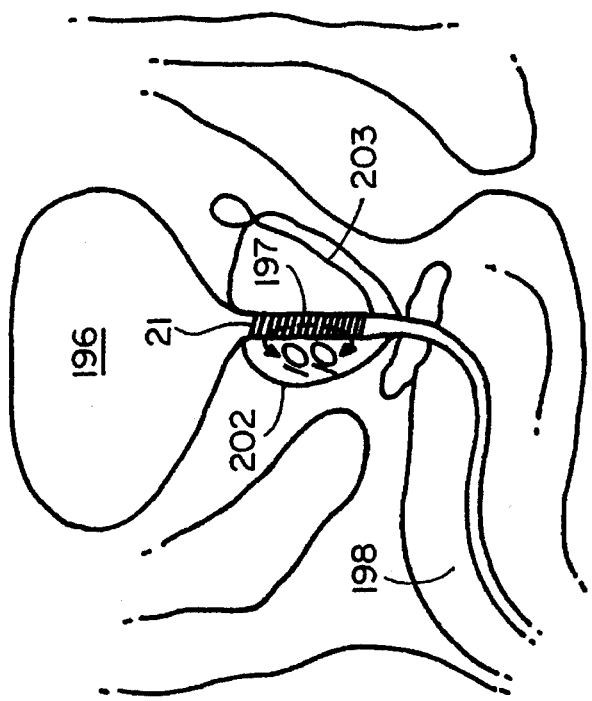
*FIG_9*
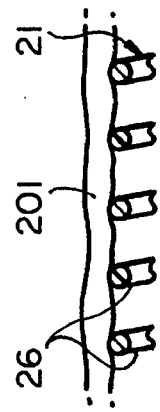
*FIG_10*
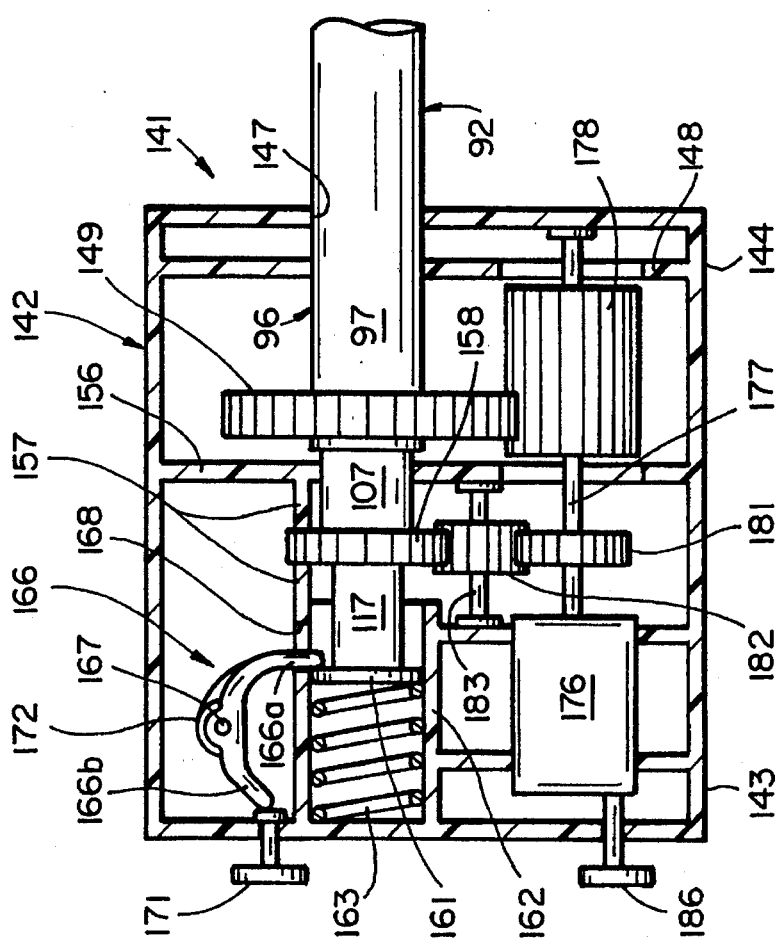
*FIG_8*

STENT FOR USE IN PROSTATIC URETHRA, APPARATUS AND PLACEMENT DEVICE FOR SAME AND METHOD

This invention pertains generally to stents and, more particularly, to biocompatible stents for placement in the portion of the urethra extending through the prostate.

Benign prostatic hypertrophy or hyperplasia (BPH) is a common medical problem associated with aging men. Thermal and other surgical procedures have heretofore been utilized for treating BPH. An edematous response in the urethral tissue may accompany many of the thermal therapies. The resulting swelling can cause partial or complete obstruction of the prostatic urethra and may not subside for several weeks so as to permit normal urinary function. During this time, it is customary to catheterize the patient using a Foley-type catheter. Although expandable metal stents have been heretofore provided for transurethral insertion into the prostatic urethra, these stents are intended to provide only palliative relief and often must be removed at some point in the future. There is, therefore, a need for a stent, an apparatus and device for placing the stent and a method which overcomes these disadvantages.

In general, it is an object of the present invention to provide a biocompatible stent for placement in the prostatic urethra as part of a thermal procedure involving the prostate.

Another object of the invention is to provide a stent of the above character which is absorbable by the body of the patient.

Another object of the invention is to provide a stent of the above character which contains a medicament to aid in the healing of the prostate.

Another object of the invention is to provide a stent of the above character which has a configuration which facilitates its retention within the prostatic urethra before absorption by the body of the patient.

Another object of the present invention is to provide an apparatus and device and a method for placing the stent in the prostatic urethra.

Additional objects and features of the invention will appear from the following description from which the preferred embodiments are set forth in detail in conjunction with the accompanying drawings.

FIG. 1 is a side-elevational view of an apparatus of the present invention which includes a placement device with a stent mounted thereon.

FIG. 2 is a cross-sectional view taken along the line 2—2 of the apparatus of FIG. 1.

FIG. 3 is a side-elevational view of the placement device and stent of FIG. 1.

FIG. 4 is a side elevational view, partially cut away, of a portion of the stent of FIG. 3 in an expanded condition.

FIG. 5 is an enlarged view, partially cut away, taken along the lines 5—5 of the placement device of FIG. 3.

FIG. 6 is a cross-sectional view taken along the line 6—6 of the placement device of FIG. 3.

FIG. 7 is a cross-sectional view taken along the line 7—7 of the placement device of FIG. 3.

FIG. 8 is an enlarged view, partially cut away and rotated 45°, taken along the lines 8—8 of the placement device of FIG. 3.

FIG. 9 is an illustration of the stent of the present invention in place within the prostatic urethra.

FIG. 10 is an enlarged view, partially cut away and rotated 90°, taken along the lines 10—10 in FIG. 9.

In general, the stent of the present invention is for introduction into a portion of a urethra in a body of a patient. The urethra extends through a prostate and is formed by a wall having a diameter. The stent includes a longitudinally-extending body made from a material adapted for absorption by the body of the patient. The longitudinally-extending body has an expanded condition in which the body has a predetermined diameter greater than the diameter of the portion of the urethra extending through the prostate. The longitudinally-extending body is formed with a plurality of coils along the length thereof adapted to engage the wall of the urethra when the longitudinally-extending body is in the expanded condition. The longitudinally-extending body is provided with spaces between the coils to permit the wall of the urethra to extend therein and serve to anchor the longitudinally-extending body to the wall.

More in particular, stent 21 of the present invention is formed from a flexible elongate tubular member or body 22 made of a biocompatible material (See FIGS. 3 and 4). This biocompatible material can be a polymer capable of being absorbed by the body of the patient when the stent is placed within the portion of the urethra extending through the prostate. Suitable polymers capable of being absorbed by an organism include polylactic acid, polyglycol acid, polyglactin, polydioxane, polyglyconate, copolymer of trimethyl carbonate and glycolyd and copolymer of polyglycolic acid or polyactic acid with T-caprolactone. Stent body 22 can alternatively be made of other materials such as a protein suspension formulated to be gradually absorbed over a time period appropriate to the normal time, which may be several weeks, for healing of the prostate following a thermal procedure. Cylindrical body 22 has a length ranging from 1.5 to 4.0 centimeters and has proximal and distal extremities 23 and 24. Body 22 has a coil-like configuration, in this regard being formed from a plurality of coils 26 longitudinally spaced apart along the length of body 22, and is formed with a flow passage 27 extending therethrough. Although the coils are shown as being circular in cross section, the coils can be formed with cross-sections which are rectangular, oblong, triangular or otherwise and be within the scope of the present invention.

Stent body 22 further includes an extension 28 which extends longitudinally from the proximal most coil 26 in a proximal direction. A proximal tang 31 extends radially inwardly from the end of extension 28. A distal tang 32 extends radially inwardly from the distal most coil 26. Body 22 has a memory of a first radially expanded position, illustrated in FIG. 4, in which stent 21 has a first predetermined diameter which is greater than the diameter of the portion of the prostatic urethra in which the stent is to be placed. More specifically, body 22 has an outer diameter ranging from 0.15 to 0.50 inch when in this first expanded position. When stent 21 is in its expanded position, there is a generous and substantial distance between adjacent coils which ranges from 1 to 2 millimeters. Body 22 can be radially reduced in size to a second position in which the diameter of the body is less than the first predetermined diameter such as, for example, approximately 0.10 to 0.19 inch.

Apparatus 36 of the present invention includes a rigid sheath or probe 37 which can be of a suitable type and size as, for example, 16 to 24 French (See FIGS. 1 and 2). Probe 37 can be formed of a suitable material such as stainless steel and is provided with proximal and distal extremities 38 and 39 and has a flow passage or lumen 42 extending from the proximal extremity to the distal extremity. Distal extremity 39 has a forwardly and upwardly extending curved surface 43 through which an inclined opening 44 extends (see FIG. 1). Distal extremity 39 is also provided with a portion 39a of increased thickness to provide a blunt end for probe 37 to adapt it to enter into the urethra in the prostate during a procedure. Probe 37 is provided with a hub 47 mounted on proximal extremity 38 thereof. Hub 47 is provided with petcocks 48 on opposite sides of the hub. A locking ring 51 is rotatably mounted on hub 47 and is provided with a handle 52 which is adapted to be utilized for mounting proximal extremity 38 of probe 37 as hereinafter described.

A bridge 61 is mounted on probe 37. Bridge 61 consists of a bridge housing 62 formed of a suitable material such as metal or a polycarbonate or other plastic. A sleeve 63 is mounted therein which can be formed of a suitable material such as stainless steel. The distal extremity of sleeve 63 is provided with a male threaded extension 66 which is adapted to mate with locking ring 51 provided on proximal extremities 38 of probe 37. Sleeve 63 is provided with a cylindrical bore (not shown) extending therethrough which is adapted to receive a conventional cystoscope 71.

Cystoscope 71 typically is a reusable, direct vision device and is provided with a cylindrical stainless steel optical tube 72 which is adapted to fit with a slip fit within sleeve 63 of bridge 61. Such an optical tube 72 is well known to those skilled in the art and contains a plurality of rod-like optical elements (not shown) to provide excellent viewing capabilities at distal extremity 73 of tube 72. The tube 72 is sized so that it can readily fit within lumen 42 of probe 37 and also so that distal extremity 73 is disposed immediately to the rear of curved surface 43 at the distal extremity of probe 37. A fitting 74 is provided on the proximal extremity of tube 72 and carries a port 77 which can be connected to a light guide tube (not shown) connected into a conventional light source (not shown). An eye piece 78 is carried by fitting 74.

Bridge 61 is also provided with a downwardly depending bifurcation 81 provided with a hole or channel 82 formed in a gradual curve so that it is in alignment with the proximal extremity of lumen 42 provided in probe 37.

Apparatus 36 further includes a placement device 91 for use with probe 37, bridge 61 and cystoscope 71 in placing stent 21 within the portion of the urethra extending through the prostrate of the patient. Placement device 91 includes an elongate element or member in the form of tubular assembly 92 having proximal and distal extremities 93 and 94. As illustrated in FIGS. 5–7, tubular assembly 92 includes an outer tubular elongate member in the form of sleeve 96 made from any suitable material such as stainless steel and having a wall thickness ranging from 0.006 to 0.035 inch. Sleeve 96 includes proximal and distal extremities 97 and 98 and has a central bore 99 extending longitudinally between the proximal and distal extremities. Proximal extremity 97 is formed with a plurality of slits or slots 101 aligned in pairs longitudinally spaced apart along the length of the proximal extremity. Slots 101 of each pair are generally aligned in a plane transverse to the longitudinal axis of sleeve 96 and each subtend an equal angle less than 180°. Adjacent pairs of slots 101 are angularly offset by approximately 90° about the longitudinal axis of sleeve 96. As can be appreciated by those skilled in the art, adjacent pairs of aligned slots 101 permit bending of sleeve 96 about respective transverse axes extending at approximate right angles to each other and to the longitudinal axis of sleeve 96 so as to allow sleeve 96 to be rotatable about its longitudinal axis when in a bent position.

Tubular assembly 92 further includes a second tubular elongate member in the form of mandrel 106 made from any suitable material such as stainless steel and having a wall thickness ranging from 0.003 to 0.010 inch. Mandrel 106 has proximal and distal extremities 107 and 108 and has a central bore 109 extending longitudinally between the proximal and distal extremities thereof. The mandrel slidably and rotatably extends through central bore 99 of sleeve 96 between proximal and distal extremities 97 and 98 of the sleeve. Proximal extremity 107 of mandrel 106 is provided with a plurality of aligned slits or slots 111 substantially similar to slots 101 of sleeve 96. Distal extremity 108 of the mandrel has a blunt bull nose 112. A first tubular liner 113 made from any suitable plastic material such as polyester or nylon is concentrically carried about mandrel 106 so as to extend between the mandrel and sleeve 96 and permit smooth relative rotation and sliding between the mandrel and the sleeve.

A third tubular elongate member in the form of tubular cutter 116 is included within tubular assembly 92. Cutter 116 is made from any suitable material such as stainless steel and has proximal and distal extremities 117 and 118. Proximal extremity 117 is provided with a plurality of aligned slits or slots 121 substantially similar to slots 101. The end of distal extremity 118 is beveled inwardly to form an annularly extending edge 122. Cutter 116 extends through central bore 109 of mandrel 106 between proximal and distal extremities 107 and 108 of the mandrel. A second tubular liner 123, substantially similar to first tubular liner 113, is concentrically carried about cutter 116 so as to extend along the length of tubular assembly 92 between mandrel 106 and cutter 116 and facilitate relative longitudinal and rotational movement between the mandrel and cutter.

Placement device 91, and more specifically mandrel 106, includes stent receiving means adapted to receive stent body 22 in its second or reduced configuration. In this regard, distal extremity 108 of mandrel 106 extends beyond distal extremity 98 of sleeve 96 a distance approximately equal to the length of stent body 22. Mandrel 106 is provided with first and second longitudinally spaced apart holes 126 and 127 for respectively receiving proximal and distal tangs 31 and 32 of body 22. First hole 126 inclines radially inwardly as it extends through mandrel 106 so as to have a beveled lower edge 128 which circumferentially engages proximal tang 31. Second tubular liner 123 and cutter 116 are provided with respective slots 131 and 132 through which the proximal tang extends. After stent 21 has been configured in its second reduced position, tangs 31 and 32 are secured within tubular assembly 92 by any conventional means such as heating the tangs once they extend within tubular assembly 92 so that when pressed against the inside of the tubular assembly they expand to preclude their removal from holes 126 and 127. Outer sleeve 96 is enlarged at distal extremity 98 so as to provide a keyway 133 which extends over extension 28 of stent body 22 for reasons hereinafter described.

Placement device 91 includes handle means in the form of a handle 141 mounted on proximal extremity 93 of tubular assembly 92. Handle 141 has a housing 142 made from any suitable material such as plastic and formed with proximal and distal end portions 143 and 144. Proximal extremity 93 of tubular assembly 92 snugly extends through an opening 147 in distal end portion 144 of the housing and is further secured within the housing by a rib 148 which circumferentially engages proximal extremity 97 of sleeve 96. A gear 149 is rigidly secured to the outside of proximal extremity 97. Proximal extremity 107 of mandrel 106 extends beyond the proximal extremity of sleeve 96 and is further laterally secured within housing 142 by a rib 156 and longitudinally secured within the housing by a rib 157. A gear 158 is rigidly secured to the proximal end of mandrel 106. Proximal extremity 117 of cutter 116 extends rearwardly from the proximal extremity of mandrel 106 and is provided with a flange 161 at its proximal end which is slidably disposed within a longitudinally extending barrel 162 provided in housing 142.

Means is carried by handle 141 and secured to proximal extremity 93 of placement device 91 for releasing stent 21 from the placement device. In this regard, a coil spring 163 is disposed within barrel 162 and engages flange 161 so as to urge cutter 116 in a distal or forward direction. Cutter 116 is locked in a proximal position against the force of coil spring 163 by a latch 166 which is mounted within housing 142 for pivotal movement about a pin 167. Latch 166 has a locking end 166a which extends through a hole 168 in the side of barrel 162 so as to engage flange 161 and retain cutter 116 in its proximal position. Flange 166 has a second or trigger end 166b which is engagable by a release button 171 extending through proximal end portion 143 of housing 142. The locking end of latch 166 is urged against flange 161 by a retention spring 172 coiled about pin 167.

The release means of placement device 91 further includes means for rotating sleeve 96 and mandrel 106 in opposite directions about the longitudinal axis of tubular assembly 92 so as to cause stent body 22 to expand to its first position. In this regard, a spring driver 176 mounted within housing 142 has a spindle 177 which extends longitudinally from the spring driver in the distal direction. A first elongate drive gear 178 is mounted to spindle 177 between ribs 148 and 156 and engages sleeve gear 149. A second drive gear 181 is mounted to spindle 177 between first drive gear 178 and spring driver 176 and engages an idler gear 182 mounted on a spindle 183 connected to housing 142 and extending in a direction parallel with spindle 177. Idler gear 182 in turn engages mandrel gear 158.

Handle 141 is adapted to advance distal extremity 94 of tubular assembly 92 through channel 82 of bridge 61 into lumen 42 of probe 37. In this regard, tubular assembly 92, having stent 21 mounted to distal extremity 108 of mandrel 106 and distal extremity 98 of sleeve 96 in the manner discussed above, is inserted through channel 82 until housing 142 engages bifurcation 81 of bridge 61. Tubular assembly 92 is disposed in lumen 42 of probe 37 adjacent to and below optical tube 72 of cystoscope 71. The tubular assembly of placement device 91 is sized so that stent 21 extends beyond probe 37 when the placement device is so mounted to probe 37.

In operation and use, apparatus 36 and placement device 91 of the present invention can be used in connection with a procedure to treat BPH such as that described in copending application Ser. No. 08/191,258 filed Feb. 2, 1994. FIG. 9 illustrates a portion of a body of a human having a bladder 196 with a urethra 197 extending therefrom and through a penis 198. Urethra 97 is formed by a wall 201 and passes through the prostate 202 situated below bladder 196. The ejaculatory duct 203 joins the urethra 197 within the prostate.

During the procedure described in copending application Ser. No. 08/191,258 filed Feb. 2, 1994, now U.S. Pat. No. 5,549,644, probe 37, bridge 61 and cystoscope 71 can be utilized for receiving an ablation device for creating lesions within the prostate so as to reduce its size. As pan of this procedure, a sleeve or sheath of a suitably insulating material such as NYLON 11 is provided which includes a large lumen. A tip of formed insulation such as NYLON 11 is formed by the application of heat to the distal extremity of the sheath. The tip is provided with a bore therein which is in registration with the lumen of the sheath. A needle electrode is slidably mounted in the lumen of the sheath and extends through the bore of the tip. The needle electrode is formed of a suitable material such as a nickel titanium alloy having superelastic properties. The needle electrode is caused to penetrate the urethral wall closely followed by the insulating sheath. Penetration of the urethral wall in this manner causes tenting of the urethral wall which tenting continues as the needle and insulating sheath are advanced into the tissue of the prostate. Radio frequency energy is supplied to the needle electrodes disposed within the prostatic tissue. The retractable shield or sheath provided on the needle electrodes serve to protect the urethral wall from damage from the radio frequency energy. Lesions are created in the prostatic tissue by the needle electrodes. Such a procedure may result in swelling of the prostatic tissue and cause the urethra to become partially or totally occluded. Upon completion of the procedure, the ablation device can be removed from probe 37 and placement device 91 having stent 21 mounted on the distal extremity thereof inserted through channel 82 of bridge 61 into lumen 42 of probe 37 in the manner discussed above.

Cystoscope 71 can be utilized for properly placing stent 21 within the prostatic urethra. Once the stent has been placed within the partially or totally occluded portion of the prostatic urethra, handle button 186 on placement device 91 is pressed to cause spring driver 176 and first and second drive gears 178 and 181 to rotate sleeve 96 and mandrel 106 in opposite directions. This relative angular rotation of sleeve 96 and mandrel 106 causes the sleeve to force proximal tang 31 against edge 128 formed within hole 126 of the mandrel and thereby sever proximal tang 31 from stent body 22. Further relative rotation of the sleeve and the mandrel causes proximal extremity 23 of stent body 22, as trapped within keyway 133 of sleeve 96, to move in an opposite angular direction about the longitudinal axis of the stent relative to distal extremity 24 of the stent body. The forces exerted on stent body 22 by placement device 91 during expansion of stent 21 are sufficient to overcome the opposing frictional forces exerted on coils 26 of the stent body by urethral wall 201. As stent 21 is so moved from its second reduced position to its first expanded position, any reduction in longitudinal size of the stent is accommodated by sleeve 96 sliding distally along tubular liner 123 relative to mandrel 106. Elongate first drive gear 178 permits sleeve gear 149 to be continually driven as it moves longitudinally along the first drive gear.

After stent 21 has expanded outwardly to engage wall 201 of the portion of urethra 197 extending through prostate 202, actuation of release button 171 causes latch 166 to rotate about pin 167 against retention spring 172 and release flange 161 from its locked position within barrel 162. Coil spring 163 drives cutter 116 in a distal direction to cause beveled edge 122 of cutter 116 to shear distal tang 132 and so release the distal extremity 24 of stent 21 from placement device 91. Removal of placement device 91 from urethra 197 causes extension 28 of stent body 22 to come out of keyway 133 and releases the stent body from placement device 91.

As so placed within the prostatic urethra, as illustrated in FIG. 9, stent 21 has a sufficient coil strength to oppose the tendency of the edema to force urethra wall 201 inward and thus maintains a flow passageway through urethra 197. The substantial spacing between coils 26 of stent body 22 facilitates retention of stent 21 within the urethra. In this regard, this spacing permits the tissue of urethral wall 201 to extend radially and bulge inwardly within the coils and thus increase the portion of the surface of each coil in circumferential engagement with the wall of the urethra. As can be appreciated by those skilled in the art, the increased friction forces from this increased surface engagement area increases the friction forces between stent 21 and the urethral wall and also hinders longitudinal movement of the stent within the urethra.

The material of stent body 22 is absorbed by the normal absorbative action of the tissue and circulatory system of the patient and/or the action of the urine passing over stent 21. Coils 26 of the stent, however, are sized so that the stent retains sufficient rigidity for maintaining a flow passage through the prostatic urethra despite the gradual reduction in the size of the coils from the body's absorption of the stent material. More specifically, the outward radial forces of the stent are always greater than the compressive forces being exerted on the stent by the walls of the urethra. These compressive forces also decrease as swelling of the urethra tissue subsides.

The stent of the present invention permits the patient to avoid the discomfort, inconvenience and costs associated with catherization and physician removal of the catheter. In addition, the stent can contain medicaments such as antibiotics to aid in the healing of the tissues of the urethra. These medicaments can be released over time as the material of the stent is absorbed.

Although the method of the present invention includes driving proximal and distal extremities 23 and 24 of stent body 22 in opposite angular directions so as to expand the stent to a predetermined radial diameter sufficient to free the stent from placement device 91 and form a flow passage in the prostatic urethra, it should be appreciated that a stent which has a memory so as to automatically retain its expanded condition upon its release within the prostatic urethra would be within the scope of the invention. Furthermore, it should be appreciated that stents having other configurations would also be suitable and within the scope of the present invention. Such stents could have substantial openings and/or protuberances in the sides thereof for increasing the retention forces on the stent and could, for example, have a braided configuration or be molded in a tubular form with openings extending through the sides of the stent.

In addition, although the method of the invention has been discussed in connection with a transurethral ablation device of the type described in copending application Ser. No. 08/191,258 filed Feb. 2, 1994, it should be appreciated that stent 21 can be used with other procedures for treating BPH, including, for example, thermal therapies such as microwave energy, laser treatment, cryogenic surgery and other methods using radio frequency treatment.

In view of the foregoing, it can be seen that a biocompatible stent has been provided for placement in the prostatic urethra as part of a thermal procedure involving the prostate. The stent is absorbable by the body of the patient and contains a medicament to aid in the healing of the prostate. The stent is provided with a configuration which facilitates its retention within the prostatic urethra before absorption by the body of the patient. An apparatus and device and a method for placing the stent in the prostatic urethra have also been provided.

What is claimed is:

1. A device for introducing a stent into a portion of a urethra extending through a prostate by use of a probe having proximal and distal extremities with a passageway extending from the proximal extremity to the distal extremity, a scope mounted on the proximal extremity of the probe and extending into the passageway along a first longitudinal axis, the device comprising an elongate element having proximal and distal extremities and extending along a second longitudinal axis, the elongate element having a transverse size adapted to permit the elongate element to be removably disposed in the passageway adjacent the scope with the second longitudinal axis spaced apart from the first longitudinal axis, stent securing means carried by the distal extremity of the elongate element adapted to secure the stent to the distal extremity of the elongate element, handle means mounted on the proximal extremity of the elongate element adapted to advance the distal extremity of the elongate element with the stent thereon into the passageway of the probe so that the elongate element is disposed adjacent the scope with the second longitudinal axis spaced apart from the first longitudinal axis and at least a portion of the stent extending beyond the distal extremity of the probe into said portion of the urethra and means carried by the handle means actuable to release the stent from the stent securing means into said portion of the urethra.

2. The device of claim 1 in combination with the stent wherein said portion of the urethra is formed by a wall having a diameter, the stent comprising a longitudinally-extending body made from a material adapted for absorption by the body of the patient, the longitudinally-extending body having an expanded condition in which said body has a predetermined diameter greater than the diameter of the wall, the longitudinally-extending body being formed with a plurality of coils along the length thereof adapted to engage the wall when the longitudinally-extending body is in the expanded condition, the longitudinally-extending body being provided with spaces between the coils to permit the wall to extend therein and serve to anchor the longitudinally-extending body to the wall.

3. The device of claim 2 wherein the spaces between coils range from 1 to 2 millimeters.

4. The device of claim 1 wherein the body has an elasticity sufficient to permit the body to move to a reduced condition having a diameter at least 20% less than the predetermined diameter.

5. An apparatus for use with a medical device for treating benign prostatic hypertrophy of a prostate to care for a portion of a urethra extending through the prostate, comprising a probe having proximal and distal extremities and a passageway extending from the proximal extremity to the distal extremity, a scope mounted on the proximal extremity of the probe and extending into the passageway, the passageway having a transverse size adapted to permit the medical device to be removably disposed in the passageway while the scope is mounted on the proximal extremity of the probe, a stent having an expanded condition in which the stent has a predetermined diameter and a reduced condition in which the stent has a diameter less than the predetermined diameter, an elongate element having proximal and distal extremities, the transverse size of the passageway permitting the elongate element to be removably disposed in the passageway while the scope is mounted on the proximal extremity of the probe, stent securing means carried by the distal extremity of the elongate element for securing the stent in the reduced condition to the distal extremity of the elongate element when the elongate element is free of the probe, handle means mounted on the proximal extremity of the elongate element for advancing the distal extremity of the elongate element with the stent thereon through the passageway to the distal extremity of the probe and means mounted on the proximal extremity of the elongate element actuable to release the stent from the stent securing means into said portion of the urethra.

6. The apparatus of claim 5 wherein the stent has first and second end portions and the elongate element extends along a longitudinal axis and wherein the means mounted on the proximal extremity of the elongate element actuable to release the stent includes means carried by the elongate element to engage the first end portion of the stent and cause relative angular rotation of the first and second end portions of the stent about the longitudinal axis.

7. The apparatus of claim 6 wherein the means carried by the elongate element to engage the first end portion of the stent and cause relative angular rotation of the first and second end portions of the stent includes an additional elongate element concentrically carried by the first named elongate dement for rotation about the longitudinal axis.

8. A method for treating benign prostatic hypertrophy of a prostate having a portion of a urethra extending through the prostate by use of a medical device, an elongate element having a distal extremity and a cylindrical stent having opposite first and second end portions, comprising introducing the medical device into the urethra, treating the prostate with the medical device to create lesions in the prostate, securing at least the first and second end portions of the stent to the distal extremity of the elongate element, introducing the distal extremity of the elongate element into the urethra releasing the stent from the elongate element so as to place the stent in said portion of the urethra and introducing a scope into the urethra to permit continuous viewing of said portion of the urethra between the treating and releasing steps.

9. The method of claim 8 further comprising the step of viewing the introduction of the medical device into the urethra and the placement of the stent in said portion of the urethra with the scope.

10. A method for treating benign prostatic hypertrophy of a prostrate having a portion of the urethra formed by a wall extending through the prostate utilizing a probe, a scope extending along a first longitudinal axis, a medical device and a cylindrical stent extending along a second longitudinal axis, comprising the steps of introducing the probe into said portion of the urethra, inserting the scope into the probe for viewing the interior of the urethra, inserting the medical device into the probe adjacent the scope, performing a procedure on the prostate with the medical device to create lesions in the prostate, removing the medical device from the probe, inserting the stent into the probe adjacent the scope in place of the medical device with the second longitudinal axis spaced apart from the first longitudinal axis, viewing the stent with the scope while introducing the stent into said portion of the urethra and releasing the stent in said portion of the urethra to permit the stent to engage the wall of the urethra and thus inhibit partial occlusion or total occlusion of said portion of the urethra.

11. The method of claim 10 wherein the wall in said portion of the urethra has a diameter and the stent has a predetermined diameter which is greater than the diameter of the wall, further comprising the step of reducing the diameter of the stent prior to the inserting step so that the diameter of the stent is less than the diameter of the wall.

12. The method of claim 10 wherein the performing step includes introducing a needle electrode into the prostate and supplying radio frequency energy to the needle electrode to create a lesion in the prostate.

13. The method of claim 12 wherein the performing step includes introducing an insulating sleeve concentrically carried about the needle electrode into the prostate to protect the wall while radio frequency energy is being supplied to the needle electrode.

14. A device for introducing a stent into a portion of a urethra extending through a prostate by use of a probe having proximal and distal extremities with a passageway extending from the proximal extremity to the distal extremity, a scope mounted on the proximal extremity of the probe and extending into the passageway along a first longitudinal axis, the device comprising an elongate element having proximal and distal extremities and extending along a second longitudinal axis, the elongate element having a transverse size adapted to permit the elongate element to be removably disposed in the passageway adjacent the scope with the second longitudinal axis spaced apart from the first longitudinal axis, stent securing means carried by the distal extremity of the elongate element adapted to secure the stent to the distal extremity of the elongate element, handle means mounted on the proximal extremity of the elongate element adapted to advance the distal extremity of the elongate element with the stent thereon into the passageway of the probe so that the elongate element is disposed adjacent the scope with the second longitudinal axis spaced apart from the first longitudinal axis and means mounted on the proximal extremity of the elongate element actuable to release the stent from the stent securing means into said portion of the urethra.

15. The device of claim 14 wherein the stent has first and second end portions and wherein the means mounted on the proximal extremity of the elongate element actuable to release the stent includes means carried by the elongate element adapted to engage the first end portion of the stent and cause relative angular rotation of the first and second end portions of the stent about the second longitudinal axis.

16. The device of claim 15 wherein the means carried by the elongate clement adapted to engage the first end portion of the stent and cause relative angular rotation of the first and second end portions of the stent includes an additional elongate element concentrically carried by the first named elongate element for rotation about the second longitudinal axis.

17. A method for treating benign prostatic hypertrophy of a prostrate having a portion of the urethra formed by a wall extending through the prostate utilizing a probe, a scope extending along a first longitudinal axis, a medical device and a cylindrical stent extending along a second longitudinal axis, comprising the steps of introducing the probe into the urethra, inserting the scope into the probe for viewing the interior of the urethra, inserting the medical device into the probe adjacent the scope, performing a procedure on the prostate with the medical device to create lesions in the prostate, removing the medical device from the probe, inserting the stent into the probe adjacent the scope in place of the medical device with the second longitudinal axis spaced apart from the first longitudinal axis and releasing the stent from the probe into said portion of the urethra to permit the stent to engage the wall of the urethra.

18. The method of claim 17 further comprising the step of viewing the stent in the urethra with the scope.

\* \* \* \* \*